(12) United States Patent
Sloth et al.

(10) Patent No.: US 9,393,381 B2
(45) Date of Patent: Jul. 19, 2016

(54) COVER UNIT FOR USE WHEN INSERTING A PUNCTURE DEVICE IN AN ANATOMICAL STRUCTURE SUCH AS A VEIN OR AN ARTERY AND FOR MAINTAINING SAID PUNCTURE DEVICE IN THE ANATOMICAL STRUCTURE

(75) Inventors: Erik Sloth, Risskov (DK); Thomas Fichtner Bendtsen, Aarhus C (DK); Lars Knudsen, Risskov (DK)

(73) Assignee: US ENOVACOR ApS, Harlev J (DK)

( * ) Notice: Subject to any disclaimer, the term of this patent is extended or adjusted under 35 U.S.C. 154(b) by 253 days.

(21) Appl. No.: 13/996,788

(22) PCT Filed: Dec. 20, 2011

(86) PCT No.: PCT/DK2011/050504
§ 371 (c)(1),
(2), (4) Date: Jul. 3, 2013

(87) PCT Pub. No.: WO2012/083965
PCT Pub. Date: Jun. 28, 2012

(65) Prior Publication Data
US 2013/0289404 A1    Oct. 31, 2013

Related U.S. Application Data

(60) Provisional application No. 61/426,531, filed on Dec. 23, 2010.

(30) Foreign Application Priority Data

Dec. 23, 2010 (EP) ..................................... 10196787

(51) Int. Cl.
| A61F 13/00 | (2006.01) |
| A61M 25/01 | (2006.01) |
| A61M 25/02 | (2006.01) |
| A61B 8/08 | (2006.01) |

(52) U.S. Cl.
CPC ........... *A61M 25/0108* (2013.01); *A61M 25/02* (2013.01); *A61B 8/0891* (2013.01); *A61M 2025/0273* (2013.01)

(58) Field of Classification Search
CPC ................... A61B 8/0891; A61M 2025/0273; A61M 25/0108; A61M 25/02
USPC ......................................................... 72/41, 58
See application file for complete search history.

(56) References Cited

U.S. PATENT DOCUMENTS 1,532,900 A  *  4/1925  Houghland ............... 229/125.39
4,706,662 A  * 11/1987  Thompson ...................... 602/44

(Continued)

FOREIGN PATENT DOCUMENTS

| CA | 1222671 | 6/1987 |
| EP | 1552792 | 7/2005 |

(Continued)

OTHER PUBLICATIONS http://www.safersonic.com/en/productinfo/, Sterile Transducer Cover With Adhesive Strip, Safersonic.

(Continued)

*Primary Examiner* — Sanjay Cattungal
(74) *Attorney, Agent, or Firm* — James Creighton Wray; Meera P. Narasimhan

(57) ABSTRACT

A cover unit for inserting a puncture device such as a cannula in an anatomical structure such as a vein or an artery and for maintaining said puncture device in said anatomical structure, comprising a flexible film having a glue provided surface, and a removable covering layer to cover said glue provided surface, wherein said cover unit comprises a patient adherent member and a barrier member connected along a connection line, which is arranged close to a puncture site in a patient; said film being made of an ultrasound transparent material; said barrier member being provided with at least one slit or weakening line extending from next to said connection line to a side edge of the cover unit and provided in said film; and said covering layer in the barrier member is removable from the film separately from the corresponding covering layer in the patient adherent member.

20 Claims, 8 Drawing Sheets

(56) References Cited

U.S. PATENT DOCUMENTS

| | | | | |
|---|---|---|---|---|
| 6,612,990 | B1* | 9/2003 | Pruter | 600/461 |
| 2004/0049145 | A1* | 3/2004 | Flick | 602/41 |
| 2009/0181074 | A1* | 7/2009 | Makower et al. | 424/447 |

FOREIGN PATENT DOCUMENTS

| | | |
|---|---|---|
| EP | 1958569 | 5/2007 |
| GB | 2128479 | 5/1984 |
| SE | 419163 | 7/1981 |
| WO | 9300788 | 1/1993 |

OTHER PUBLICATIONS

U.S. Appl. No. 11/532,900, filed Jan. 11, 2007, Lutri.

T.J. Wigmore, et al., Effect of the implementation of NICE guidelines for ultrasound guidance on the complication rates associated with central venous catheter placement in patients presenting for routine surgery in a tertiary referral centre, British Journal of Anaesthesia, Sep. 2007, vol. 99.

Guidance on the use of ultrasound locating devices for placing central venous catheters, National Institute for Clinical Excellence, Sep. 2002, Technology Appraisal Guidance No. 49.

* cited by examiner

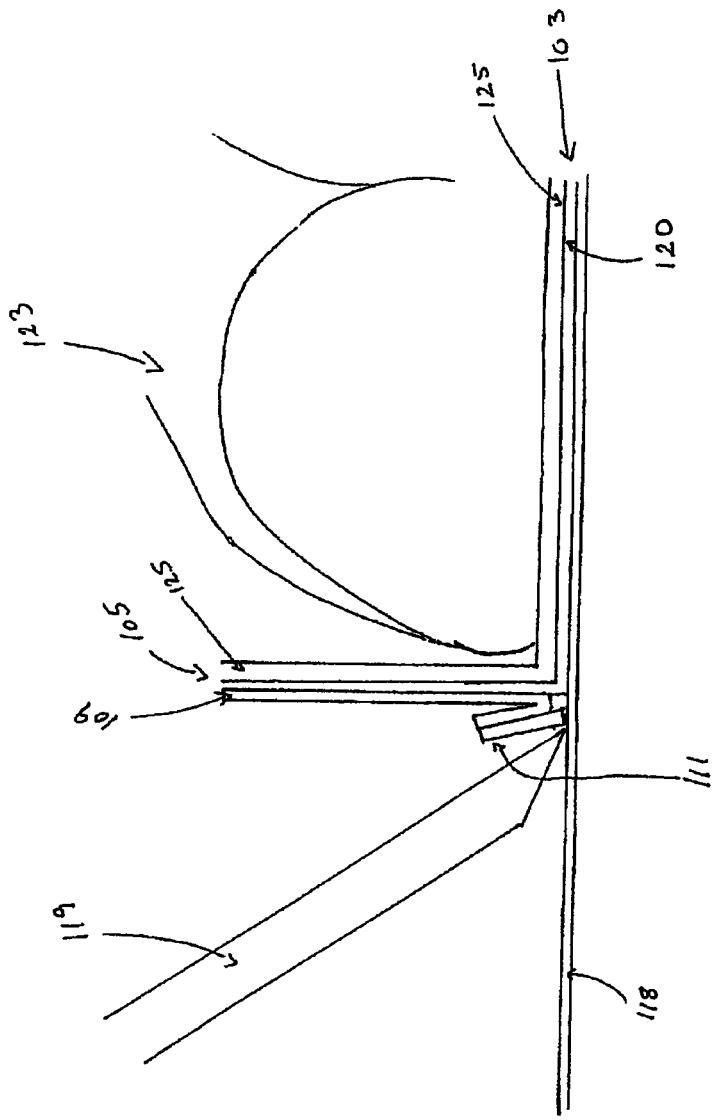

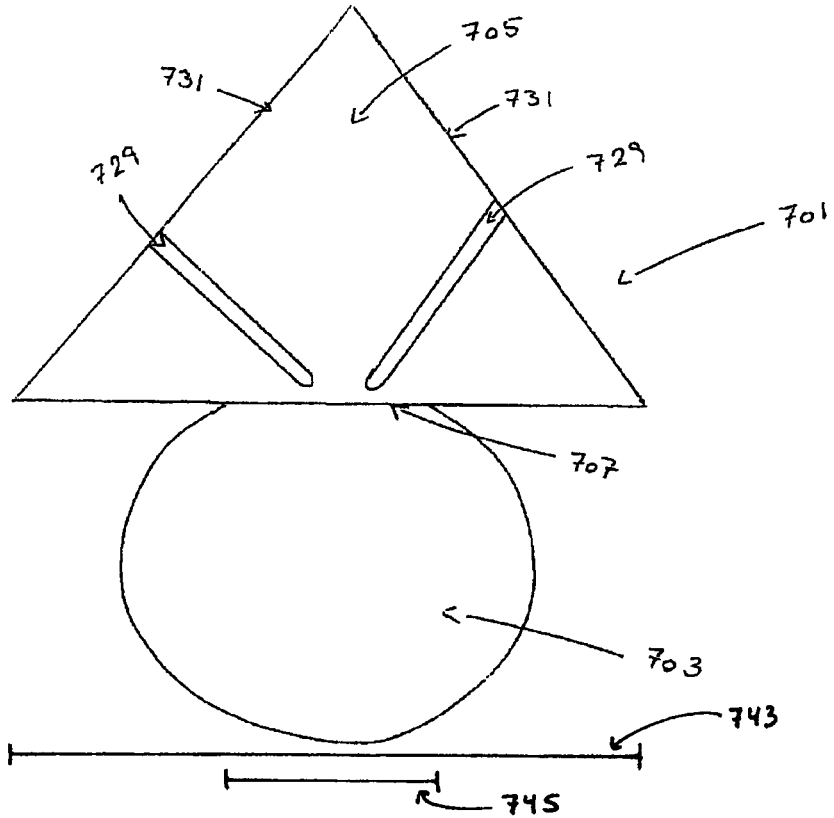
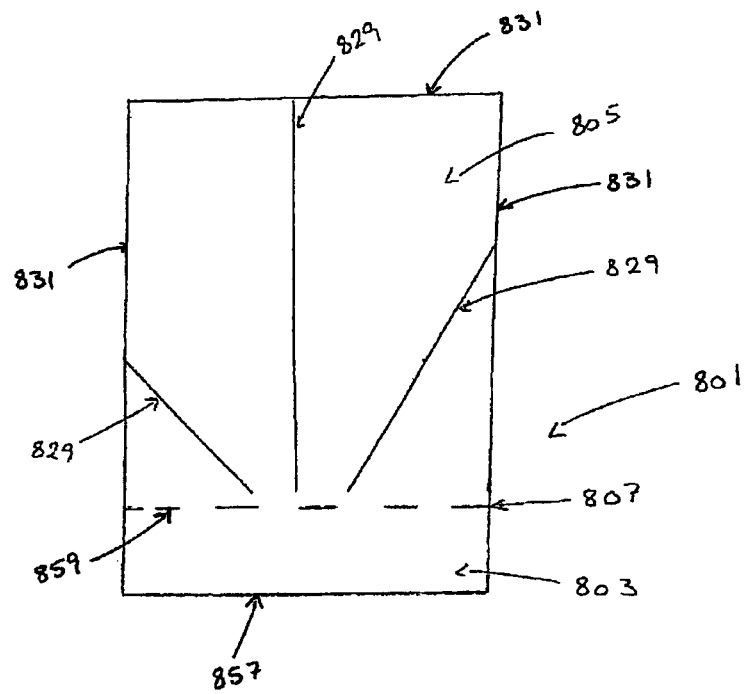

COVER UNIT FOR USE WHEN INSERTING A PUNCTURE DEVICE IN AN ANATOMICAL STRUCTURE SUCH AS A VEIN OR AN ARTERY AND FOR MAINTAINING SAID PUNCTURE DEVICE IN THE ANATOMICAL STRUCTURE

This application claims the benefit of European Application No. 10196787.5 filed Dec. 23, 2010, U.S. Application No. 61/426,531 filed Dec. 23, 2010, and PCT/DK2011/050504 filed Dec. 20, 2011, International Publication No. WO 2012/083965, which are hereby incorporated by reference in their entirety as if fully set forth herein.

FIELD OF THE INVENTION

The present invention relates to a cover unit for use when inserting a puncture device such as a cannula in an anatomical structure such as a vein or an artery and for maintaining said puncture device in the anatomical structure such as a vein or an artery. The present invention relates in particular to procedures involving visualisation using an ultrasonic device for the exact location for the puncture of the anatomical structure such as a vein or artery with a puncture device.

BACKGROUND OF THE INVENTION

Cannulas or other puncture devices are normally inserted into the vein or artery of the arms and legs with direct visualisation of the position of the vein or artery. The demand for sterility is small and thus, the skin is typically just washed or disinfected before the puncture. The puncture device is to be maintained in position after insertion. Therefore, a film is attached to the skin of the patient, close to the puncture site. The film often comprises an open-ended slit or a slot enabling the film to be arranged around the puncture device. Hereby, the puncture device is maintained in the anatomical structure.

The puncture site can be optimized and the target visualised using ultrasound. Hereby, the target is precisely localised and the puncture device can be inserted optimally into the anatomical structure such as a vein or an artery.

The advantage of using ultrasound for insertion of needles or other puncture devices into an anatomical structure of a patient is illustrated for example by the statement of the National Institute for Clinical Excellence (NICE) on the use of ultrasound locating devices for placing central venous catheters (Technology Appraisal Guidance No. 49, September 2002) by stating that "Two-dimensional imaging ultrasound guidance is recommended as the preferred method for insertion of central venous catheters into the internal jugular vein in adults and children in elective situations." A recently published study concludes that implementation of the NICE guidelines significantly reduces the number of complications observed during or after the insertion (Wigmore T J et al., Br J. Anaesth. 2007 November; 99(5): 662-5).

The position of the exact puncture site can be marked and the ultrasonic device removed before the puncture. However, minor movements of the patient often change the location for the exact procedure site. Thus, the use of real-time visualisation during the entire procedure is advantageous.

Ultrasonic gel or similar contact means is needed to obtain a proper ultrasonic image. Applying ultrasonic gel to the skin of the patient, however, makes proper attachment of the film to the skin difficult after the insertion of the puncture device. Thus, the maintaining of the puncture device in a correct position is also impaired. Hereby, the puncture device may be displaced, detached or damage the anatomical structure. Furthermore, the non-sterile ultrasonic gel may pass the skin barrier and hereby contaminate the puncture site.

OBJECT OF THE INVENTION

It is the purpose of the invention to provide a cover unit, which enables ultrasound to be used during insertion of a puncture device and hereby at the same time to solve the problems as described above.

DESCRIPTION OF THE INVENTION

The object of the invention is fulfilled with a cover unit for use when inserting a puncture device such as a cannula in an anatomical structure such as a vein or an artery and for maintaining said puncture device in said anatomical structure, comprising a flexible film having a glue provided surface, and a removable covering layer to cover said glue provided surface and where said cover unit comprises
  a patient adherent member and a barrier member being connected along a connection line dividing said cover unit into said patient adherent member and said barrier member, said connection line, in use, is arranged close to a puncture site in a patient; and
  in that said film being made of an ultrasound transparent material; and
  said patient adherent member is ultrasound transparent at least in the area adjacent to said connection line; and
  in that a glue being provided on said glue provided surface; said glue enables an ultrasonic signal to be transmitted; and
  in that said barrier member being provided with at least one slit or weakening line extending from a side edge of said cover unit towards said connection line to a position adjacent to said connection line and being provided in said film; and
  in that said covering layer in the barrier member is removable from the film separately from the corresponding covering layer in the patient adherent member.

This invention describes a cover unit for use in puncturing for targets in deeper anatomical structures by means of visualization techniques e.g. ultrasound for example at extremities e.g. arms and legs. The cover unit comprises a patient adherent member and a barrier member. A connection line divides the cover unit into the patient adherent member and a barrier member.

The cover unit can be any shape, such as triangular, circular, rectangular, squared or curved. The patient adherent member can be any shape, such as triangular, circular, rectangular, squared or curved. The barrier member can be any shape, such as triangular, circular, rectangular, squared or curved. The shape of the patient adherent member and the barrier member is not necessarily similar.

The patient adherent member is, in use, adhered to the skin of the patient, while the barrier member forms a barrier between the patient adherent member and the puncture site. The puncture site is to be interpreted as where the puncture device is to be inserted.

The barrier member is preferably arranged in a substantially upright position. An upright position is to be interpreted as a position where easy access to the puncture site is obtained. The side of the barrier member with the puncture site forms a puncture procedure area, while the side of the barrier member facing the patient adherent member forms an ultrasound scanning area. A puncture procedure space is formed above the puncture procedure area being delimited by the barrier member. An ultrasound scanning space is formed above the ultrasound scanning area being delimited by the barrier member.

An ultrasonic gel or other contact means is necessary during ultrasound scanning to obtain a proper signal. Other contact means is to be interpreted as any means known to the person skilled in the art, whereby a proper ultrasonic signal can be obtained.

If the gel or other contact means is added directly to the skin, it is insufficiently wiped off for a fixation plaster to adhere properly to the skin. This is prevented by scanning on top of the patient adherent member of the cover unit, since this is already properly attached to the skin of the patient. A new fixation plaster is not needed to be attached since the cover unit after the procedure maintains the puncture device in place. Alternatively, a new fixation plaster can be arranged on the skin by removing the cover unit along with the remains of the gel or other contact means. Hereby, the fixation plaster adheres properly to the skin of the patient.

The barrier member is of a size that provides an efficient barrier between the ultrasound scanning area and the puncture procedure area. The barrier member prevents the gel or similar contact means from interacting with the puncture site. Penetration of the skin with for example a gel in connection with the puncturing can induce stings and pain as well as the gel can result in a toxic effect.

To be able to perform an ultrasound scanning on the patient adherent member, the patient adherent member needs to be ultrasound transparent in order to obtain a proper ultrasonic signal. The patient adherent member needs only be ultrasound transparent in an area adjacent to the connection line in order for the puncture device to be properly inserted. An area adjacent to the connection line is here to be understood as the area where the ultrasound scanning is to be performed.

If the patient adherent member is not ultrasound transparent at least in the scanning area, an ultrasonic signal cannot be obtained and the anatomical structure cannot be visualised. Thus, the purpose of the cover unit cannot be fulfilled.

The barrier member and the patient adherent member can be of different sizes. In one embodiment the connection line can be provided close to the edge of the cover unit for example providing a minor patient adherent member and a major barrier member. In another embodiment the connection line is close to the middle of the cover unit, whereby the patient adherent member and the barrier member are substantially of similar size.

The entire cover unit or parts hereof comprises a flexible film having a glue provided surface, and a removable covering layer to cover said glue provided surface. As an example, only the barrier member comprises a flexible film having a glue provided surface, and a removable covering layer to cover said glue provided surface, while the patient adherent member is one adherent ultrasound transparent layer.

The cover unit comprises a flexible film with a glue provided surface. The glue provided surface is covered by a removable covering layer when not in use. The covering layer or parts of the covering layer is removed from the glue provided surface when the cover unit is to be attached to the skin of a patient. The tearing strength between the film and the covering layer is characterised by leaving the glue on the film when removing the covering layer.

Air prevents the formation of a proper ultrasonic signal. Therefore, air is to be prevented between the ultrasound device and the skin of the patient. Thus, the glue provided on the glue provided surface is to be a glue which is unable to contain air. Furthermore, the glue is unable to trap air. When attaching the film of the patient adherent member to the skin of the patient, no air will be contained between the film and the skin of the patient in the scanning area. Thus, the glue on the glue provided surface enables an ultrasonic signal to be transmitted. Any glue or adhesive, known to the person skilled in the art, capable of attaching a film to the skin of a patient and simultaneously being able to transmit an ultrasonic signal can be used. As an example the glue provided on the flexible film of Tegaderm™ from 3M™ Minnesota Mining and Manufacturing Company can be used in this invention. As another example, the adhesive attaching the cover provided by Safersonic Medizinprodukte Handles g.m.b.H., Austria (http://www.safersonic.com/en/productinfo/) to the ultrasound device can be provided as a glue in this invention. As another example, the glue provided on Steri-Drape from 3M™ Minnesota Mining and Manufacturing Company can be used in this invention. As another example, the glue provided on the barrier suction and diathermy bag from Mölnlycke Health Care, Göteborg, Sweden can be used in this invention. As another example, the glue provided on the CVK kit operation Life II from H. Dam Kaergaard A/S, Denmark can be used in this invention. Any glue with characteristics similar to the characteristics of the glue as described in the examples can be used in the invention.

A flexible film is to be understood as a film that comprises elasticity, extensibility and flexibility. Hereby, the film is able to follow the movements of the skin and remain attached for a longer time. The film can be made of any ultrasonic transparent material for example plastic, rubber, paper or silicone. As an example, the film can be made of polyurethane, elastomeric polyesters or blends hereof.

The term film is to be interpreted as any ultrasonic transparent material which can be adhered to the skin of a patient. The thickness of the film can vary depending on the specific characteristics of the material in order for the film to remain flexible as to accommodate the skin of the patient and not to affect the quality of the ultrasound image.

In one embodiment, the flexible film has a thickness of 10-45 microns.

The cover unit comprises a patient adherent member and a barrier member connected along a connection line. The connection line is, in use, arranged close to the puncture side of the patient where the skin is punctured by a puncture device. A puncture device is for example a needle, catheter, a cannule, guidewires used for venous or arterial puncture or puncture of other anatomical structures.

Patient includes humans as well as animals such as dogs, cats, horses, cattle etc.

Anatomical structure includes for example a vein, an artery, a nerve, a tendon, a nerve sheat as well as tissues such as muscle, adipose tissue etc.

In one embodiment, the connection line can be defined by a folding line for example if the barrier member and the patient adherent member are made in one piece.

In another embodiment, the connection line can be defined as an attachment line, where the barrier member is attached to the patient adherent member for example if the barrier member and the patient adherent member are two separate pieces to be combined before use. In this embodiment the barrier member and/or the patient adherent member can be provided with a small bend at the edge of the member for proper attachment to each other.

The barrier member comprises at least one slit or weakening line. The at least one slit or weakening line is provided in the film. But can also be provided in the covering layer if the at least one weakening line is not penetrative. Hereby, a barrier is provided between the ultrasound scanning site and the puncture site.

The at least one slit or weakening line enables the film to be arranged around the puncture device to maintain the puncture device in a given position.

The at least one slit or weakening line extends from next to the connection line to the side edge of the barrier member. The starting point is arranged close to the puncture site to be able to split the film on the sides of the puncture device. Thus, the at least one slit or weakening line extends from the side edge of the cover unit towards the connection line. The at least one slit or weakening line extends to a position adjacent to the connection line. By adjacent is to be understood that the at least one slit or weakening line ends directly at the connection line or in a distance to the connection line of 0.1-10 mm, preferably 1-7 mm, more preferred 2-5 mm, or most preferred 2-3 mm.

The extension of the at least one slit or weakening line can be perpendicular to the connection line or any given angle between perpendicular and substantially parallel. The weakening lines can easily be torn open to form a slit, when they are to be used.

When more weakening lines or slits are provided in the barrier member, the puncture device can be arranged in the slit or the torn weakening line, whichever of the more weakening lines or slits are closest to the actual puncture site. Hereby, the barrier member can be more smoothly arranged around and/or on either side of the puncture device.

The at least one weakening line can be a straight line or a curved line.

The covering layer on the barrier member is removed separately from the covering layer on the patient adherent layer. This is advantageous since the covering layer can be removed from the patient adherent layer and the cover unit attached to the skin of the patient without the glue provided surface of the barrier member to be exposed. If the glue provided surface of the barrier member is exposed, as well, it could easily attach to itself or the skin of the patient in an undesirable manner. Furthermore, the covering layer is normally needed to retain an intact barrier due to the at least one slit or weakening line.

In an advantageous embodiment, the covering layer is stiffer than the film and supports the barrier member whereby it can be arranged in a substantially upright position. Hereby, easy access to the puncture site is gained.

As an example of manufacturing, the cover unit can be manufactured by multilayer constructions. The individual cover units are hereafter punched out. The cover units can comprise different features, as described elsewhere in the description, in each layer. The features can be added before or after adjoining the layers.

In a further advantageous embodiment, said cover unit further comprises a support layer, said support layer is glued to said film on an opposing surface of said covering layer.

On the opposite side of the film, opposing the covering layer a support layer can be provided to stabilize both the patient adherent member and barrier member. Preferably, the support layer is a removable support layer and can easily be removed from the film. The support layer is attached to the film with a material of a tearing strength leaving the glue or similar attaching material on the support layer when removed from the film. The support layer is stiffer than the film and supports the film. Hereby, the film can be attached smoothly to the skin of the patient.

The support layer can further support the barrier member. Hereby, the barrier member can be arranged in a substantially upright position. Upright is to be interpreted as easily gaining access to the puncture site.

A support layer is useful when the material of the film is thin and highly elastic, and when the film can be difficult to control with regard to moveability and attachment to the skin after the covering layer is removed.

The barrier member comprises at least one slit or weakening line. The at least one slit or weakening line is provided in the film. However, the at least one slit or weakening line can also be provided in the support layer. If the at least one slit or weakening line is also present in the support layer, the covering layer is to be present on the barrier member during the puncturing procedure. Hereby, a barrier is provided between the ultrasound scanning site and the puncture site. If the at least one weakening line is not penetrative it can be present in all three layers without destroying the barrier effect of the barrier member.

In a further advantageous embodiment, said support layer in the barrier member is removable from the film separately from the corresponding support layer in the patient adherent member.

In one embodiment, the support layer on the barrier member can be removed separately from the support layer on the patient adherent layer. Hereby, for example the support layer can be maintained on the barrier member, while removed on the patient adherent member. The barrier member maintains a given stiffness, which can be helpful in order to control the barrier member during the ultrasound scanning and puncture procedure.

In an advantageous embodiment, said patient adherent member further comprises a gel-removing layer, where said gel-removing layer is ultrasound transparent. The gel-removing layer is arranged on top of the film opposing the glue-provide side.

In one embodiment, the gel-removing layer can be arranged between the film and the support layer of the entire cover unit or only part hereof. Advantageously, the gel-removing layer is only arranged between the support layer and the film of the patient adherent member.

The gel-removing layer is ultrasound transparent and thus, ultrasonic scanning can be performed through both the gel-removing layer and the film. The gel or similar contact means is added to the top of the gel-removing layer before scanning. The gel-removing layer is after scanning removed from the film, whereby the remaining gel or similar contact means is removed as well and the film comprises a clean surface.

Advantageously, the gel-removing layer comprises a flap or a flange at one of the edges which can be seized, in order to easily remove the gel-removing layer.

The gel-removing layer can be made from a material similar to the film or of a different material. The gel-removing layer is partly or fully attached to the film leaving no trace of the attachment on the film after detaching.

In a further advantageous embodiment, said support layer is separated into a patient supporting border part along one or more edges of said patient adherent member and at least one patient adherent supporting part. In a still further advantageous embodiment said support layer is separated into a first barrier supporting part in said barrier member and at least one second barrier supporting part.

Dividing the support layer into parts on either the patient adherent member or the barrier member enable one or more parts to be removed while one or more parts are left on the cover unit. Hereby, selected sites can be supported by the support layer.

A patient supporting border part or supporting frame on the patient adherent member can be left after removing the central part of the support member. The patient supporting border part can be of varying dimensions, however, leaving sufficient space for proper ultrasonic scanning. The patient supporting border part stabilises the patient adherent member during scanning and prevents the film from detaching from the skin of the patient.

In one embodiment, the second barrier supporting part of the support layer of the barrier member closest to the connection line is removed. If the film is transparent it is possible to observe the exact position of the ultrasonic device in relation to the puncture site during the puncture procedure. Furthermore, the first barrier supporting part of the support layer left supports the other part of the barrier member making the holding and controlling of the barrier member easier during the puncture procedure.

In a further embodiment, the first barrier supporting part remaining of the support layer is a border along one or more edges of the barrier member in order to stabilise barrier member.

In a further embodiment, the part remaining of the support layer is a barrier supporting border part along one or more edges of the barrier member including a barrier supporting border part along the connection line. Hereby, the barrier member can be stabilised. Depending on the stiffness of the support layer, the barrier member can be in an upright position with regard to the patient adherent member.

In a further advantageous embodiment, at least a part of said support layer is ultrasound transparent.

If the support layer is ultrasound transparent at least at the patient adherent member or at least at the scanning area of the patient adherent member, the support layer or parts of the support layer need not to be removed before the ultrasonic scanning procedure. Thus, scanning gel or similar contact means is provided to the ultrasound transparent part of the support layer before scanning. The support layer removes the remains of the gel or similar contact means when removing the support layer or ultrasound transparent parts hereof.

In a further advantageous embodiment, said covering layer on said barrier member is provided with a flap.

The flap can easily be seized, whereby the covering layer can be removed from the film easily and quickly. This is advantageous for example when the covering layer of the barrier member is not removed until the patient adherent member has been attached to the skin of the patient and the puncture device has been inserted.

In one embodiment, the flap is provided by the covering layer being larger than the size of the film. Hereby, the covering layer automatically forms a flap, which can be seized for removing the covering layer.

The flap can be provided at any suitable site of the cover unit such as on the barrier member or the patient adherent member. The flap can be arranged either close to the connection line or along one of the edges of the cover unit. Alternatively, the flap can be provided as a fold in the covering layer and/or the support layer on the surface of the cover unit.

In a further embodiment, the support layer is provided with a flap. This flap can be formed and be provided in positions as described above.

In a still further advantageous embodiment, said at least one slit or weakening line provides a U- or V-shaped cut-out.

A U-shape or a V-shape makes the task of arranging the film of the barrier member with regard to the puncture device easier. For example, a cannula comprise a larger top part than tube part and the V-shape or U-shape enable the film to be arranged easily around and/or along the top part of the cannula.

In a further advantageous embodiment, said at least one weakening line comprises one or more indentations or perforations.

The at least one weakening line can be formed by one or more perforations enabling the film and possibly the support layer or cover layer to be torn by hand. The size, shape and distance between the perforations can vary between different weakening lines or within a weakening line. The size, shape and distance between the perforations are dependent upon the material to be torn.

The at least one weakening line can comprise one or more indentations. If the at least one weakening line only comprises one depression, the depression extends substantially along the entire weakening line. If the at least one weakening line comprises two or more indentations, the size, shape and distance between the indentations can vary between different weakening lines or within a weakening line. The size, shape and distance between the indentations are dependent upon the material to be torn.

In a further advantageous embodiment, at least one shortening line extends across said barrier member, preferably substantially parallel to said connection line.

When at least one shortening line is provided from one edge of the barrier member to the other edge i.e. across said barrier member, the size of the barrier member can be adjusted by tearing along the shortening line. For example, the barrier member can be torn along a substantially parallel shortening line after scanning if only a small part of material is needed for maintaining the puncture device in place. Alternatively, the barrier member can be torn, if the cover unit is to be arranged at a place with minor space.

The at least one shortening line can comprise perforations and indentations as described above.

The at least one shortening line can be a straight line or a curved line.

In another advantageous embodiment, the at least one shortening line extends from one side of the barrier member to the other side, non-parallel to the connection line i.e. the shortening line can start at the one side of the barrier member close to the connection line and extend to the other side of the barrier member but ends close to the upper edge of the barrier member, where the upper edge of the barrier member being opposite of the connection line.

In a still further advantageous embodiment, said covering layer of said barrier member comprises at least two parts being separately removable.

Hereby, selected parts of the glue-provided film surface can be exposed and attached to the skin of the patient, while the remaining parts of the barrier member remain covered with the covering layer.

In one embodiment, the covering layer is separated into two parts arranged parallel to the connection line. The first covering part of the covering layer closest to the connection line is removed after the puncture procedure and the barrier member is then partly attached to the skin of the patient. A parallel weakening line provided in the film, and possibly in the support layer if this is present, enables the second covering part of the barrier member to be removed. Alternatively, the non-attached part of the barrier member can be cut off.

In a further advantageous embodiment, at least a part of said barrier member is transparent, preferably said part of said barrier member next to said connection line.

The entire barrier member comprising a film and a covering layer can be transparent or a part of said barrier member can be transparent. Furthermore, the entire support layer or a part of said support layer can be transparent. Hereby, the exact position of the ultrasonic device can be followed in relation to the puncture site. Thus, the puncture device is simpler and quicker to insert into an anatomical structure.

Often the ultrasonic device comprises a marking defining the centre of the ultrasonic device. The marking illustrates the position corresponding to the position visualised in the centre of the ultrasound image. If the barrier member or part of the barrier member is transparent, the marking of the ultrasonic device is visible to the person inserting the puncture device, and the position of the puncture device with regard to the anatomical structure can quickly and with less discomfort of the patient be determined. Hence, the puncture device can be inserted correctly with regard to the anatomical structure.

Alternatively, both the support layer and the film of the barrier member or parts hereof are transparent. Then the covering layer has to be removed before the exact position of the ultrasonic device can be followed in relation to the puncture site.

In a further advantageous embodiment, the width of said barrier member at said connection line is larger than the width of said patient adherent member.

This prevents gel or similar contact means from entering the puncture site from the scanning site by by-passing the ends of the connection line. The puncture site is thus not contaminated with non-sterile gel or similar contact means.

In a further advantageous embodiment, one or more indentations are provided in said connection line.

The indentations in the connection line enable the patient adherent member and the barrier member to be separated after use. Hereby, only the barrier member maintains the puncture device in the correct position. This is advantageous for example in positions with narrow spacing. It can further be advantageous for humans with small extremities such as children.

If the connection line only comprises one depression, the depression extends substantially along the entire connection line. If the connection line comprises two or more indentations, the size, shape and distance between the indentations can vary dependent upon the material.

In a further advantageous embodiment, at least two types of glue are provided on said glue provided surface. Thus, two, three, four, five etc. glues, i.e. different types of glue, can be provided on the glue provide surface. Different properties of the different types of glues can, thus, be utilized.

In an advantageous embodiment, the different types of glue can be provided on different areas of the cover unit. As an example, one type of glue is provided to the area adjacent to the connection line, where the glue is unable to contain air making the area ultrasound transparent. A different type of glue can then be provided to the remaining area of the cover unit, where this glue is advantageous for attaching to the skin of a patient for a sustained period of time. Alternatively, a further type of glue can be provided to areas of the glue provided surface which attaches to the puncture device when in use.

This invention further describes a method for inserting a puncture device such as a cannula in an anatomical structure such as a vein or an artery using ultrasound and a cover unit, as described above, having a patient adherent member and a barrier member being connected along a connection line dividing said cover unit into said patient adherent member and said barrier member; said cover unit comprising a flexible film having a glue provided surface and a removable covering layer, where said flexible film comprises at least one slit or weakening line comprising the steps of:

locating a puncture site;

washing or disinfecting said puncture site;

removing said covering layer of said patient adherent member;

optionally removing said covering layer of said barrier member;

attaching said patient adherent member to the skin of a patient, hereby arranging said connection line of said cover unit close to said puncture site;

providing gel or similar contact means on said film of said patient adherent member;

scanning through said film at said patient adherent member using an ultrasonic device for visualisation of an anatomical structure;

inserting a puncture device at said puncture site into said anatomical structure such as an artery or a vein being guided by ultrasonic visualisation of said anatomical structure;

removing said gel or similar contact means from said film;

optionally, removing said covering layer of said barrier member from said film in case it is not removed simultaneously with said covering layer of said patient adherent member;

optionally in case a weakening line is provided, tearing said weakening line in order to form a slit;

arranging said film of said barrier member around or on either side of said puncture device.

The barrier member of the cover unit is used to provide a barrier between the ultrasound scanning area and the puncture site. At the beginning of the puncture procedure, the site to be punctured is located, washed or disinfected.

Then the covering layer of the patient adherent member is removed and the cover unit attached to the skin of the patient. Alternatively, the covering layer of both the patient adherent member and the barrier member is removed before attaching the patient adherent member to the skin of the patient. However, this is only possible if the at least one weakening line is not penetrating the film; else the barrier effect would be damaged.

Then gel or similar contact means is provided on top of the film of the patient adherent member.

Then the ultrasonic device scans on top of the film of the patient adherent member and a puncture device is inserted into an anatomical structure such as an artery or a vein at the puncture site close to the connection line. The puncture device is inclinedly inserted. Thus, the puncture device is detected by the ultrasonic device and the correct placement of the puncture device can be obtained.

Then the gel or similar contact means is removed from the surface of the film by wiping. Alternatively, a gel-removing layer can be removed.

Then the covering layer of the barrier member is detached from the film. Then eventually, a slit can be made by tearing at least one of said at least one weakening lines. This slit can for some embodiments be torn before detaching the covering layer from the film.

Then the film of the barrier member is arranged around or on either side of the puncture device.

Following this method for inserting a puncture device into an anatomical structure by using a cover unit and an ultrasonic device enables the puncture device to be correctly inserted even in structures difficult to reach. Furthermore, the method decreases the time of work necessary, and the comfort of the patient is also improved by preventing puncture devices from being incorrectly inserted. In addition, the cover unit is able to maintain the puncture device in an appropriate position after insertion of the puncture device though ultrasonic measurements were used by attaching the flexible film of the barrier member to the skin, and preferably to parts of the puncture device.

When attaching the patient adherent member to the skin, it is important that air is not trapped between the film and the skin, especially in the scanning area since ultrasonic measurements are hindered by air.

In one option, the covering layer is removed from the film of the barrier member before the cover unit is attached to the skin of the patient. The glue-provided surface of the film is, thus, exposed and can easily be adhered to the skin of the patient after the puncture device is inserted. The film is most often to be held manually in order to provide a barrier between the scanning area and the puncture site. If the covering layer is removed from the barrier member before puncture of the skin, the film is provided with at least one weakening line in order to maintain the sterility of the puncture site.

In another option, the covering layer is removed from the film of the barrier member after the puncture device is inserted into the anatomical structure. The covering layer can act in a supportive manner to the film, enabling the barrier member to be self supportive forming a barrier in a substantially upright position between the scanning area and puncture site without the need of manual holding of the barrier member.

The film can comprise one or more weakening lines. By tearing the weakening lines is to be understood that one or more weakening lines can be torn depending on which weakening line is closest to the puncture site and/or if more puncture devices have been inserted.

In a further advantageous method said cover unit further comprises a support layer and where the method further comprises the steps of:
  removing said support layer from said patient adherent member after attacking said cover unit to the skin of said patient; and
  removing said support layer from said barrier member after inserting said puncture device.

The barrier member of the cover unit is used to provide a barrier between the ultrasound scanning area and the puncture site. At the beginning of the puncture procedure, the site to be punctured is located, washed or disinfected.

Then the covering layer of the patient adherent member is removed and the cover unit is attached to the skin of the patient. Alternatively or in addition, the covering layer of both the patient adherent member and the barrier member is removed before attaching the patient adherent member to the skin of the patient.

Then the support layer or part of the support layer is removed from the patient adherent member in order to expose an ultrasound transparent surface. If the support layer is ultrasound transparent, this step is not needed. Alternatively, the support layer or parts of the support layer is detached from the film of the barrier member.

Then gel or similar contact means is provided on top of the film of the patient adherent member.

Then the ultrasonic device scans on top of the film of the patient adherent member and a puncture device is inserted into an anatomical structure such as an artery or a vein at the puncture site close to the connection line. The puncture device is inclinedly inserted. Thus, the puncture device will be detected by the ultrasonic device and the correct placement of the puncture device can be obtained.

After insertion of the puncture device, the support layer or remaining parts of support layer, if not removed earlier, are removed.

Then the gel or similar contact means is removed from the surface of the film by wiping. Alternatively, a gel-removing layer can be removed.

Then covering layer and/or support layer of the barrier member is detached from the film. Then eventually, a slit can be made by tearing at least one of said at least one weakening lines. This slit can for some embodiments be torn before detaching the covering layer and/or support layer from the film.

Then the film of the barrier member is arranged around or on either side of the puncture device.

When the cover unit is provided with a support layer, it is easier to arrange the patient adherent member to the skin of the patient. Furthermore, the support layer on the barrier member can act as a support enabling the barrier member to be positioned in a substantially upright position without the need of manually holding the barrier member for it to form a barrier between the ultrasound scanning area and the puncture procedure area.

In an alternative method, the support layer is ultrasound transparent at least for the patient adherent member or for part of the patient adherent member. Then the support layer of the patient adherent member is not removed prior to the insertion of the puncture device. The support layer is then removed after the insertion of the puncture device and hereby the contact means, such as an ultrasonic gel, are removed as well.

In a further advantageous method, said cover unit further comprises a support layer and where the method further comprises the steps of:
  removing said support layer from said patient adherent member and parts of said support layer from said barrier member after attaching said cover unit to the skin of said patient; and
  removing remaining parts of said support layer from said barrier member after inserting said puncture device.

The support layer of the barrier member can be divided into two or more parts such as a barrier supporting border part, i.e. a first barrier supporting part along one or more edges of the barrier member, and a central part, i.e. a second barrier supporting part. When the central part is removed before scanning, the barrier supporting border part supports the barrier member in forming a barrier with no need of being manually held. Advantageously, removing the central part enables the ultrasonic device to be observed through the barrier member. The barrier supporting border part is removed after the insertion of the puncture device.

In an alternative method, the support layer on said patient adherent member comprises more parts such as a patient supporting border part along one or more edges of the patient adherent member and a central part, i.e. a patient adherent supporting part. Removing only the central part before scanning enables the patient supporting border part to support the continued attachment of the film to the skin of the patient. The patient supporting border part is removed after the insertion of the puncture device.

In an alternative method, both the support layer on the patient adherent member and the barrier member comprises more parts such as a supporting border and central parts. Only the central parts are removed before scanning while the patient supporting border part and the barrier supporting border part are removed after insertion of the puncture device.

In a further advantageous method, said cover unit further comprises a gel-removing layer and removing said gel-removing layer when removing said gel or similar contact means.

The gel-removing layer removes remains of gel or similar contact means from the surface of the cover unit. Hence, the remains need not be wiped from the surface of the cover unit.

In a further advantageous method, said puncture device is inclinedly inserted. Hereby, the puncture device is easier to insert correctly into the anatomical structure.

DESCRIPTION OF THE DRAWING

FIG. 1B illustrates a side-view of a first embodiment of a cover unit in use,
FIG. 7 illustrates a seventh embodiment of a cover unit
FIG. 8 illustrates an eight embodiment of a cover unit

DETAILED DESCRIPTION OF THE INVENTION

Figure 1A:
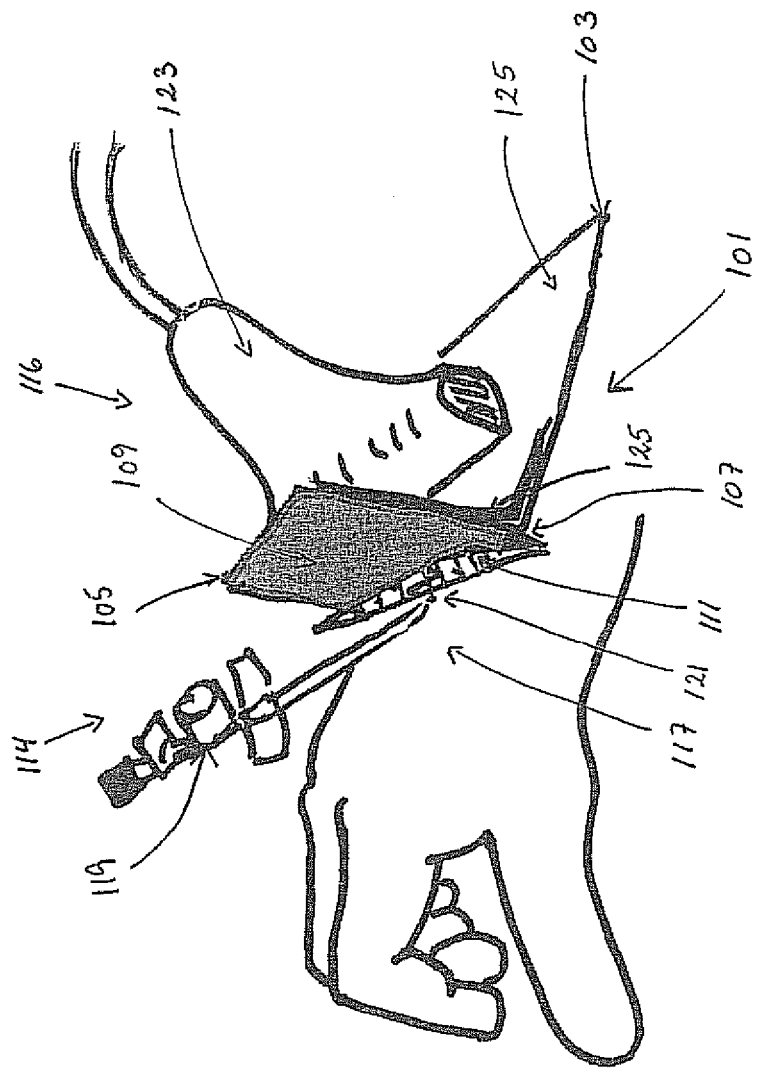
FIG. 1A illustrates a first embodiment of a cover unit in use.

FIG. 1A and FIG. 1B illustrates a cover unit 101 comprising a patient adherent member 103 and a barrier member 105 connected along a connection line 107. The barrier member 105 comprises a covering layer 109 comprising a flap 111 next to the connection line. The barrier member 105 further comprises a film 125. In this embodiment the film 125 is a relative stiff material, which enables the barrier member 105 to be at a position upright to the patient adherent member 103 whereby the puncture site 121 is easily accessible. The barrier member 105 defines a puncture procedure area 114 and a scanning area 116.

The patient adherent member 103 is attached to the wrist 117 of a patient. A cannula 119 is to be inserted through the skin into an anatomical structure such as a vein or an artery at the puncture site 121. An ultrasonic device 123 is arranged at the top of the patient adherent member 103.

As illustrated in FIG. 1B, the patient adherent member 103 is attached directly to the skin 118 of the patient. The film 125 comprises glue 120 allowing an ultrasonic signal to be transmitted. No air is present between the film 125 and the skin 118 of the patient. Hence, visualisation of anatomical structures close to the puncture site 121 using ultrasound is possible.

With the first embodiment the puncturing procedure takes place as follows: The wrist 117 is washed and/or disinfected. Then the covering layer of the patient adherent layer 103 is removed and the patient adherent layer 103 attached to the skin of the patient. The barrier member 105 is arranged in an upright position allowing puncturing. Gel is placed on the film 125 and the ultrasonic device 123 starts scanning. The cannula 119 is inserted into an anatomical structure guided by the ultrasonic scanning.

After insertion, the ultrasonic device 123 is removed, and the film 125 wiped, the covering layer 109 of the barrier member 105 removed and the barrier member 105 attached to the skin for maintaining the cannula 119 in position. The covering layer 109 of the barrier member 105 is easily removed by seizing the flap 111 of the covering layer 109, which is easily accessible.

In one embodiment the covering layer 109 of the barrier member 105 is transparent to form a transparent window for coordinating the cannula 119 and the ultrasonic device 123. After the procedure, the covering layer 109 of the barrier member 105 is removed and the barrier member 105 arranged around or on either side of the inserted cannula 119.

Figure 2:
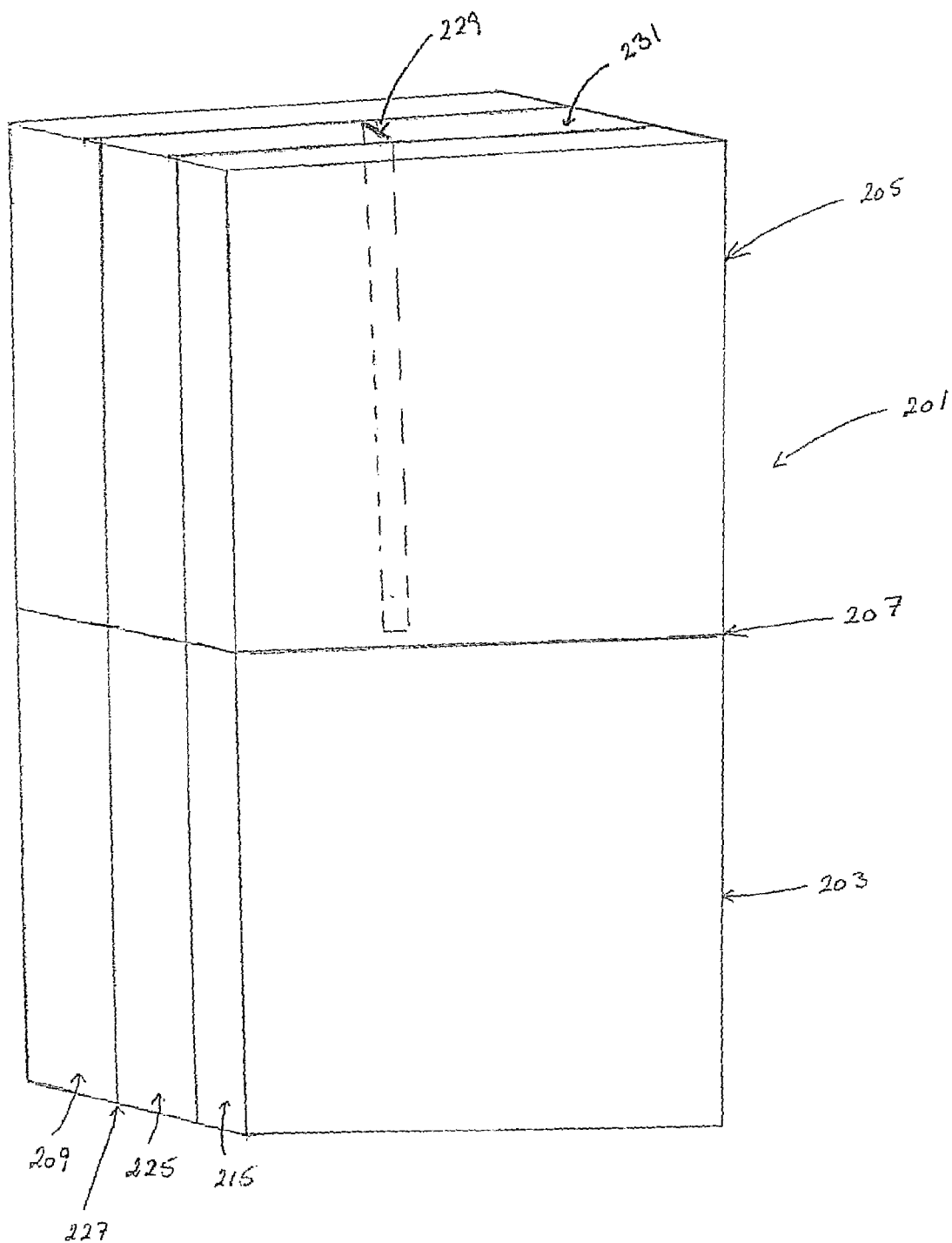
FIG. 2 illustrates a second embodiment of a cover unit.

FIG. 2 illustrates a second embodiment of a cover unit 201 comprising three material layers with an ultrasound transparent film 225 with a glue-provided surface 227, a covering layer 209 and a support layer 215. The proportion of the layers is enlarged for the purpose of illustration.

A connection line 207 separates the cover unit 201 into a patient adherent member 203 and a barrier member 205. A slit 229 is provided in the film 225, where the slit 229 extends from next to the connection line 207 and to a side edge 231 of the barrier member 205. The slit 229 divides the film 225 of the barrier member 205 into two parts which is arranged around or on either side of the puncture device to maintain the position of the puncture device.

Figure 3:
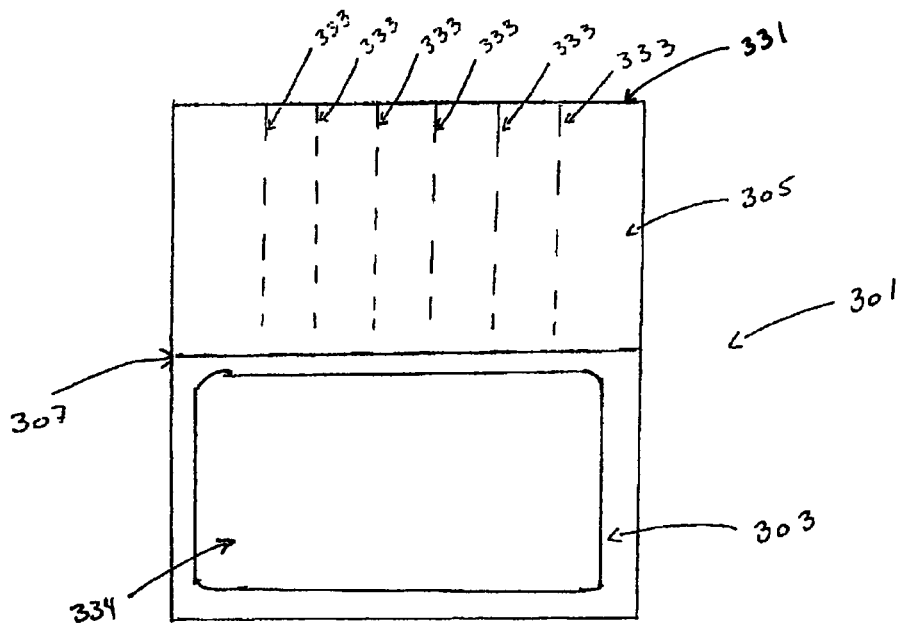
FIG. 3 illustrates a third embodiment of a cover unit.

FIG. 3 illustrates a third embodiment of a cover unit 301 comprising a patient adherent member 303 and a barrier member 305 connected along a connection line 307. The barrier member 305 is provided with six weakening lines 333. The weakening lines 333 are arranged substantially perpendicular to the connection line 307. The weakening lines 333 extend from next to the connection line 307 and to the side edge 331.

The weakening lines 333 can be provided in either the film or the film and the covering layer. However, the weakening lines 333 must not be constructed in a way where perforations are formed through the entire barrier member 305 since the barrier effect preventing contamination of the puncture site with the gel would be destroyed.

A cover unit 301 provided with six weakening lines 333 enables that the barrier member 305 to be arranged smoothly around and on either side of the puncture device. If the puncture device is inserted differently from what was expected when attaching the cover unit 301 to the skin of the patient, the puncture device is not right in front of the expected weakening line 333 or expected slit in the barrier member 305. Multiple weakening lines 333 enable the barrier member 305 to be torn in front of the actual position of the puncture device.

In this embodiment the patient adherent member 303 is provided with a gel-removing layer 334 which is ultrasound transparent. The gel-removing layer 334 can be removed after scanning with the ultrasonic device and inserting the puncture device. Hereby, it is not needed to wipe the patient adherent member 303 to remove additional gel.

Figure 4:
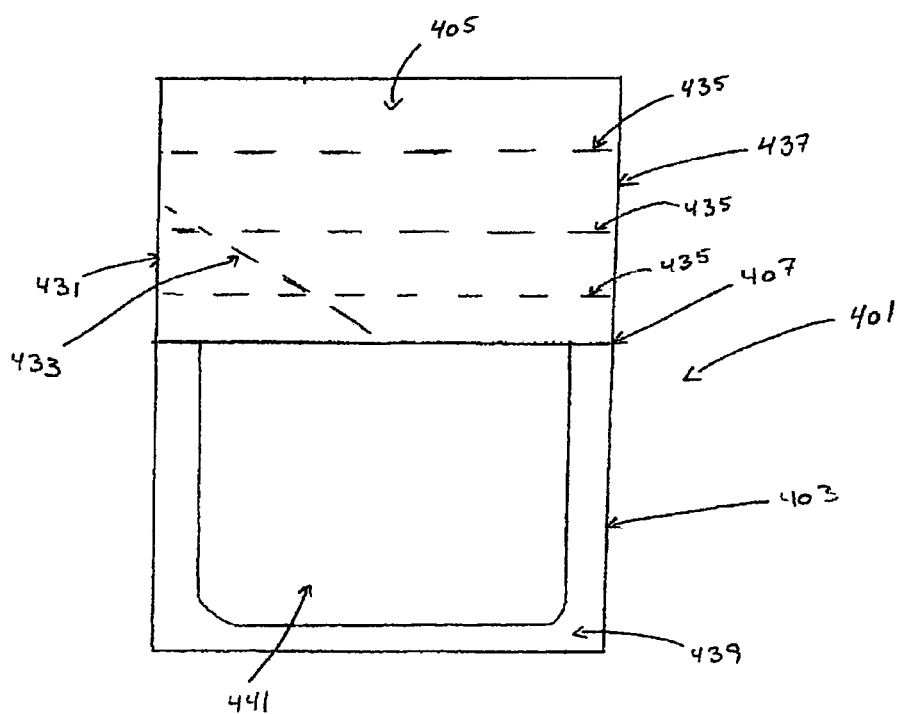
FIG. 4 illustrates a fourth embodiment of a cover unit.

FIG. 4 illustrates a fourth embodiment of a cover unit 401 comprising a patient adherent member 403 and a barrier member 405 connected along a connection line 407. The barrier member 405 is provided with one weakening line 433 and three crossing shortening lines 435. The weakening line 433 extends from next to the connection line 407 and to the side edge 431. The crossing shortening lines 435 are substantially parallel to the connection line 407 and extend from one side edge 431 of the barrier member 405 to the opposite side edge 437. The parallel shortening lines 435 can be torn to change the size of the barrier member 405.

The patient adherent member 403 comprises a two-parted support layer comprising a patient supporting border part 439 and a patient adherent supporting part 441. The two parts 439, 441 can be removed separately from one another. Advantageously, the patient adherent supporting part 441 can be removed before ultrasonic scanning leaving the patient supporting border part 439 on the patient adherent member 403. The patient supporting border part 439 stabilises the ultrasound transparent film from detaching from the skin during the puncturing procedure.

Figure 5:
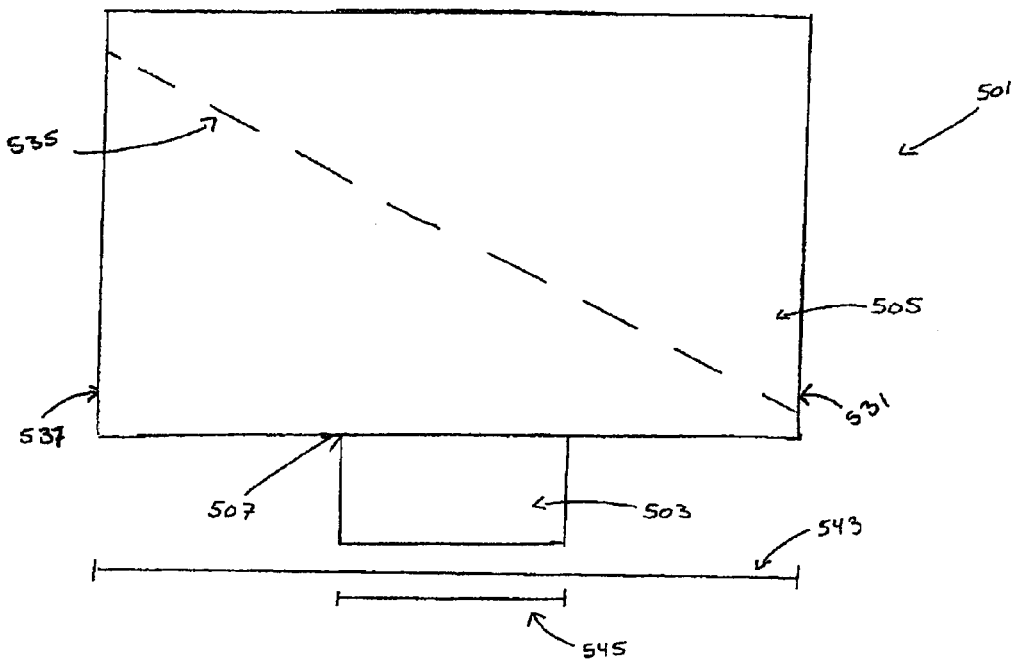
FIG. 5 illustrates a fifth embodiment of a cover unit.

FIG. 5 illustrates a fifth embodiment of a cover unit 501 comprising a patient adherent member 503 and a barrier member 505 connected along a connection line 507. The width 543 of barrier member 505 is larger than the width 545 of the patient adherent member 503. This embodiment enhances the barrier effect by preventing gel from passing the side edges 531, 537 of the barrier member 501.

The fifth embodiment further comprises a crossing shortening line 535 non-parallel to the connection line 507. This crossing shortening line 535 extends from one side edge 531 of the barrier member 505 to the opposite side edge 537. The crossing shortening line 535 can be torn to change the size of the barrier member 505.

Figure 6:
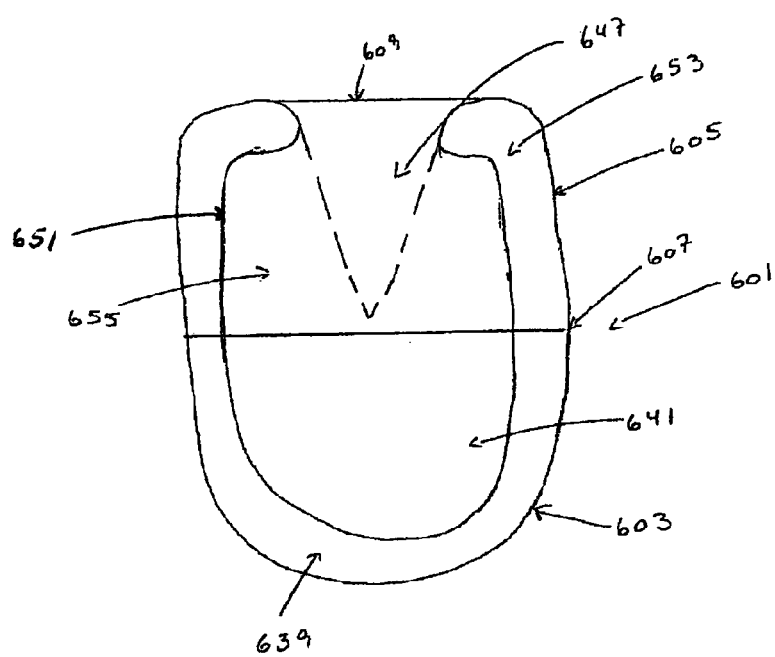
FIG. 6 illustrates a sixth embodiment of a cover unit.

FIG. 6 illustrates a sixth embodiment of a cover unit 601 comprising a patient adherent member 603 and a barrier member 605 connected along a connection line 607. The barrier member 605 is provided with a V-shaped slot 647 in the film of the barrier member 605.

The support layer 639 of the patient adherent member 603 is separated into two parts comprising a patient supporting border part 639 and a patient adherent supporting part 641. The two parts 639, 641 can be removed separately from one another. Advantageously, the patient adherent supporting part 641 can be removed before ultrasonic scanning leaving the patient supporting border part 639 on the patient adherent member 603. The patient supporting border part 639 stabilises the ultrasound transparent film from detaching from the skin during the puncturing procedure.

The support layer 651 of the barrier member 605 is separated into two parts comprising a first barrier supporting part 653 and a second barrier supporting part 655. In this embodiment, the first barrier supporting part 653 is a barrier supporting border part. The two parts 653, 655 can be removed separately from one another. Advantageously, the second barrier supporting part 655 can be removed before ultrasonic scanning leaving the first barrier supporting part 653 on the barrier member 605. The first barrier supporting part 653 stabilises the barrier member 605 during the puncturing procedure and later during the attaching of the barrier member 605 to the skin of the patient.

The barrier member 605 further comprises a covering layer 609, which is covering the glue-provided surface of the film during the puncturing procedure to maintain the effect of the barrier.

FIG. 7 illustrates a seventh embodiment of a cover unit 701 comprising a round patient adherent member 703 and a triangular barrier member 705 connected along a connection line 707. The width 743 of the barrier member 705 next to the connection line 707 is larger than the width 745 of the patient adherent member 703. This embodiment enhances the barrier effect by preventing gel from passing the side edges 731 of the barrier member 701.

The barrier member 705 is provided with two U-shaped slits 729. The U-shaped slits 729 extend from next to the connection line 707 and to the side edges 731.

FIG. 8 illustrates an eight embodiment of a cover unit 801 comprising a patient adherent member 803 and a barrier member 805 connected along a connection line 807. The barrier member 805 is provided with three slits 829. The slits 829 extend from next to the connection line 807 and to the side edges 831.

The size of the barrier member 805 and the patient adherent member 803 is unequal, and the connection line 807 is provided close to the lower edge 857 of the cover unit 801.

In this embodiment the connection line 807 is provided with indentations 859. Thus, the barrier member 805 and the patient adherent member 803 can easily be separated.

Figure 9:
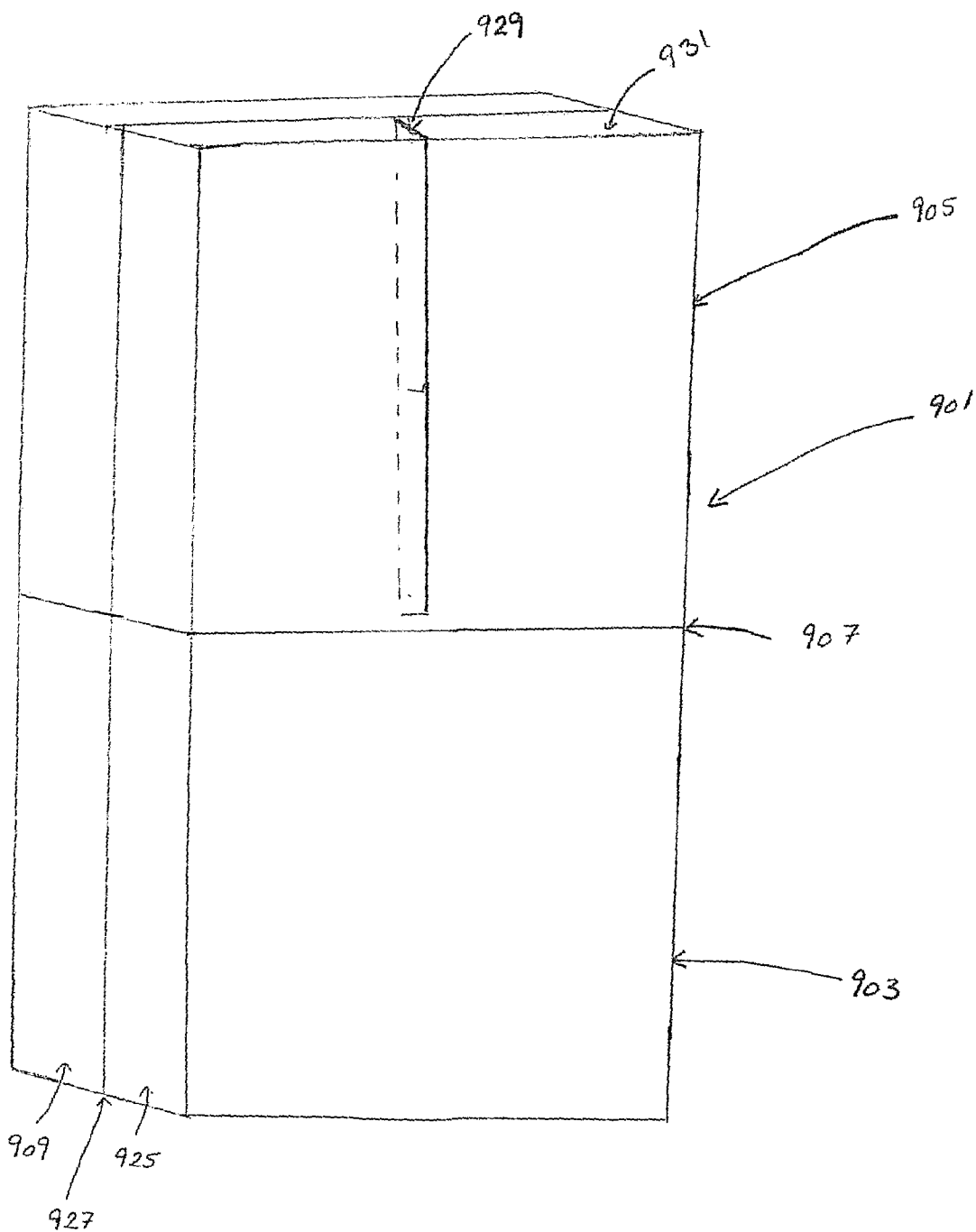
FIG. 9 illustrates a ninth embodiment of a cover unit

FIG. 9 illustrates a ninth embodiment of a cover unit 901 comprising two material layers with an ultrasound transparent film 925 with a glue-provided surface 927 and a covering layer 909. The proportion of the layers is enlarged for the purpose of illustration.

A connection line 907 separates the cover unit 901 into a patient adherent member 903 and a barrier member 905. A slit 929 is provided in the film 925, where the slit 929 extends from next to the connection line 907 and to a side edge 931 of the barrier member 905. The slit 929 divides the film 925 of the barrier member 905 into two parts which is arranged around or on either side of the puncture device to maintain the position of the puncture device.

Figure 10:
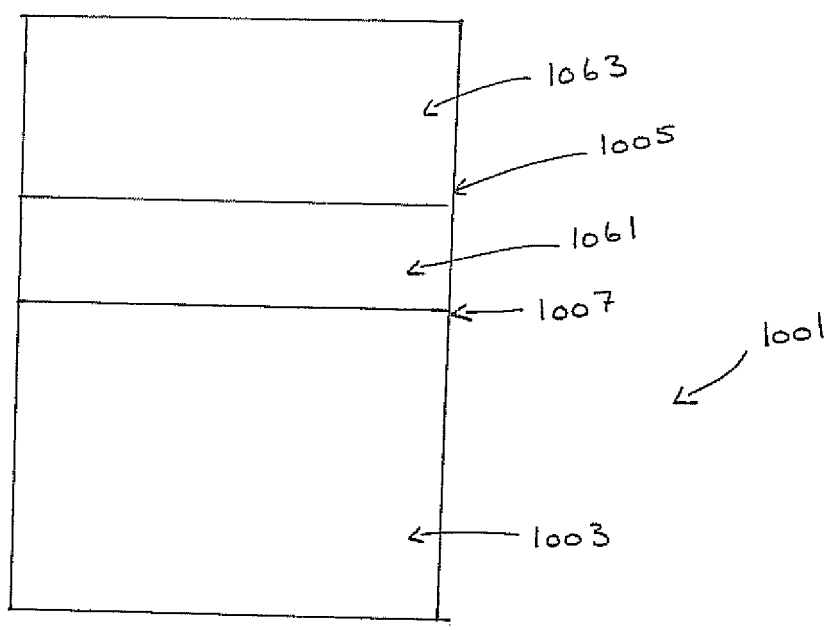
FIG. 10 illustrates a tenth embodiment of a cover unit.

FIG. 10 illustrates a tenth embodiment of a cover unit 1001 comprising a patient adherent member 1003 and a barrier member 1005 connected along a connection line 1007. The covering layer 1061, 1063 of the barrier member 1005 consist of two parts arranged parallel to the connection line 1007—a first covering part 1061 closest to the connection line 1007 and a second covering part 1063.

The first covering part 1061 can be removed after the puncture procedure and the barrier member 1005 partly attached to the skin of the patient. The second covering part 1063 can be removed for example by cutting it off.

The invention claimed is:

1. A cover unit (101) for use when inserting a puncture device (119) such as a cannula in an anatomical structure such as a vein or an artery and for maintaining said puncture device (119) in said anatomical structure, comprising a flexible film (125) having a glue provided surface (227), and a removable covering layer (109) to cover said glue provided surface (227) and wherein said cover unit (101) comprises
    a patient adherent member (103) and a barrier member (105) being connected along a connection line (107) dividing said cover unit into said patient adherent member (103) and said barrier member (105), said connection line (107), in use, is arranged close to a puncture site (121) in a patient; and
    wherein said film (125) is made of an ultrasound transparent material; and
    said patient adherent member (103) is ultrasound transparent at least in the area adjacent to said connection line (107); and
    wherein a glue is provided on said glue provided surface (227); said glue enables an ultrasonic signal to be transmitted; and
    wherein said barrier member (105) is provided with at least one slit (229) or weakening line (333) extending from a side edge (331) of said cover unit (101) towards said connection line (107) to a position adjacent to said connection line (107) and is provided in said film (125);
    wherein said covering layer (109) in the barrier member (105) is removable from the film (125) separately from the corresponding covering layer (109) in the patient adherent member (103); and
    wherein said cover unit (101) further comprises a support layer (215), said support layer (215) is glued to said film (125) on an opposing surface to said covering layer (109).

2. The cover unit (101) according to claim 1 wherein said support layer (215) in the barrier member (105) is removable from the film (125) separately from the corresponding support layer (215) in the patient adherent member (103).

3. The cover unit (101) according to claim 1 wherein said support layer (215) is separated into a patient supporting border part (439) along one or more edges of said patient adherent member (103) and at least one patient adherent supporting part (441).

4. The cover unit (101) according to claim 1 wherein said support layer (215) is separated into a first barrier supporting part (653) in said barrier member (105) and at least one second barrier supporting part (655).

5. The cover unit (101) according to claim 1 wherein at least a part of said support layer (215) is ultrasound transparent.

6. The cover unit (101) according to claim 1 wherein said covering layer (109) on said barrier member (105) is provided with a flap (111).

7. The cover unit (101) according to claim 1 wherein said at least one weakening line (333) comprises one or more indentations or perforations.

8. The cover unit (101) according to claim 1 wherein at least one shortening line (435) extends across said barrier member (105), preferably substantially parallel to said connection line (107).

9. The cover unit (101) according to claim 1 wherein said covering layer (109) of said barrier member (105) comprises at least two parts (1061, 1063) being separately removable.

10. The cover unit (101) according to claim 1 wherein at least a part of said barrier member (105) is transparent, preferably said part of said barrier member (105) next to said connection line (107).

11. The cover unit (101) according to claim 1 wherein along said connection line (107) the width (546) of said barrier member (105) is larger than the width (545) of said patient adherent member (103).

12. The cover unit (101) according to claim 1 wherein one or more indentations are provided in said connection line (107).

13. The cover unit (101) according to claim 1, wherein at least two types of glue are provided on said glue provided surface (227).

14. A method for inserting a puncture device (119) such as a cannula in an anatomical structure such as a vein or an artery using ultrasound and a cover unit (101) having a patient adherent member (103) and a barrier member (105) being connected along a connection line (107) dividing said cover unit into said patient adherent member (103) and said barrier member (105); said cover unit (101) comprising a flexible film (125) having a glue provided surface (227) and a removable covering layer (109), where said flexible film (125) comprises at least one slit (229) or weakening line (333) comprising the steps of:
- locating a puncture site (121);
- washing or disinfecting said puncture site (121);
- removing said covering layer (109) of said patient adherent member (103);
- optionally removing said covering layer (109) of said barrier member (105);
- attaching said patient adherent member (103) to the skin (118) of a patient, hereby arranging said connection line (107) of said cover unit (101) close to said puncture site (121);
- providing gel or similar contact means on said film (125) of said patient adherent member (103);
- scanning through said film (125) at said patient adherent member (103) using an ultrasonic device (123) for visualisation of an anatomical structure;
- inserting a puncture device (119) at said puncture site (121) into said anatomical structure such as an artery or a vein being guided by ultrasonic visualisation of said anatomical structure;
- removing said gel or similar contact means from said film (125);
- optionally, removing said covering layer (109) of said barrier member (105) from said film (125) in case it is not removed simultaneously with said covering layer (109) of said patient adherent member (103);
- optionally in case a weakening line (333) is provided, tearing said weakening line (333) in order to form a slit;
- arranging said film (125) of said barrier member (105) around or on either side of said puncture device (119).

15. The method according to claim 14 wherein said cover unit (101) further comprises a support layer (215) and where the method further comprises the steps of:
- removing said support layer (215) from said patient adherent member (103) after attaching said cover unit (101) to the skin (118) of said patient; and
- removing said support layer (215) from said barrier member (105) after inserting said puncture device (119).

16. The method according to claim 14 wherein said cover unit (101) further comprises a support layer (215) and where the method further comprises the steps of:
- removing said support layer (215) from said patient adherent member (103) and parts (655) of said support layer (215) from said barrier member (105) after attaching said cover unit (101) to the skin (118) of said patient; and
- removing remaining parts (653) of said support layer (215) from said barrier member (105) after inserting said puncture device (119).

17. The method according to claim 14 wherein said cover unit (101) further comprises a gel-removing layer (334) and removing said gel-removing layer (334) when removing said gel or similar contact means.

18. The method according to claim 14 wherein said puncture device (119) is inclinedly inserted.

19. A cover unit (101) for use when inserting a puncture device (119) such as a cannula in an anatomical structure such as a vein or an artery and for maintaining said puncture device (119) in said anatomical structure, comprising a flexible film (125) having a glue provided surface (227), and a removable covering layer (109) to cover said glue provided surface (227) and wherein said cover unit (101) comprises
- a patient adherent member (103) and a barrier member (105) being connected along a connection line (107) dividing said cover unit into said patient adherent member (103) and said barrier member (105), said connection line (107), in use, is arranged close to a puncture site (121) in a patient; and
- wherein said film (125) is made of an ultrasound transparent material; and
- said patient adherent member (103) is ultrasound transparent at least in the area adjacent to said connection line (107); and
- wherein a glue is provided on said glue provided surface (227); said glue enables an ultrasonic signal to be transmitted; and
- wherein said barrier member (105) is provided with at least one slit (229) or weakening line (333) extending from a side edge (331) of said cover unit (101) towards said connection line (107) to a position adjacent to said connection line (107) and is provided in said film (125);
- wherein said covering layer (109) in the barrier member (105) is removable from the film (125) separately from the corresponding covering layer (109) in the patient adherent member (103) and
- wherein said patient adherent member (103) further comprises a gel-removing layer (334), where said gel-removing layer (334) is ultrasound transparent.

20. A cover unit (101) for use when inserting a puncture device (119) such as a cannula in an anatomical structure such as a vein or an artery and for maintaining said puncture device (119) in said anatomical structure, comprising a flexible film (125) having a glue provided surface (227), and a removable covering layer (109) to cover said glue provided surface (227) and wherein said cover unit (101) comprises > a patient adherent member (103) and a barrier member (105) being connected along a connection line (107) dividing said cover unit into said patient adherent member (103) and said barrier member (105), said connection line (107), in use, is arranged close to a puncture site (121) in a patient; and
>
> wherein said film (125) is made of an ultrasound transparent material; and
>
> said patient adherent member (103) is ultrasound transparent at least in the area adjacent to said connection line (107); and
>
> wherein a glue is provided on said glue provided surface (227); said glue enables an ultrasonic signal to be transmitted; and wherein said barrier member (105) is provided with at least one slit (229) or weakening line (333) extending from a side edge (331) of said cover unit (101) towards said connection line (107) to a position adjacent to said connection line (107) and is provided in said film (125), wherein said at least one slit (229) or weakening line (333) provides a U-shaped or V-shaped cut-out, and wherein said covering layer (109) in the barrier member (105) is removable from the film (125) separately from the corresponding covering layer (109) in the patient adherent member (103).

\* \* \* \* \*